United States Patent
Enns

(10) Patent No.: US 6,926,693 B2
(45) Date of Patent: Aug. 9, 2005

(54) DRUG DELIVERY NEEDLE DEVICE

(75) Inventor: Thomas Frederick Enns, Mississauga (CA)

(73) Assignee: Benlan, Inc, Ontario (CA)

( * ) Notice: Subject to any disclaimer, the term of this patent is extended or adjusted under 35 U.S.C. 154(b) by 0 days.

(21) Appl. No.: 10/067,511

(22) Filed: Feb. 4, 2002

(65) Prior Publication Data
US 2003/0149405 A1 Aug. 7, 2003

(51) Int. Cl.⁷ .......................... A61M 5/178; A61M 5/32
(52) U.S. Cl. .................... 604/165.03; 604/177
(58) Field of Search ................ 604/171, 177, 604/180, 272, 273, 165.03, 174, 274

(56) References Cited

U.S. PATENT DOCUMENTS

| 3,856,020 | A | | 12/1974 | Kovac | |
|---|---|---|---|---|---|
| 4,235,234 | A | | 11/1980 | Whitney et al. | |
| 4,380,234 | A | | 4/1983 | Kamen | |
| 4,631,058 | A | * | 12/1986 | Raines | 604/263 |
| 4,645,495 | A | | 2/1987 | Vailancourt | |
| 4,710,176 | A | | 12/1987 | Quick | |
| 4,743,231 | A | * | 5/1988 | Kay et al. | 604/180 |
| 4,813,939 | A | * | 3/1989 | Marcus | 604/177 |
| 6,004,304 | A | | 12/1999 | Suzuki et al. | |
| 6,613,015 | B2 | * | 9/2003 | Sandstrom et al. | 604/110 |

FOREIGN PATENT DOCUMENTS

| CA | 2295831 | | 1/1999 |
|---|---|---|---|
| DE | 44 26 784 A1 | | 2/1995 |
| DE | 4426784 | * | 2/1995 |
| GB | 2 242 361 A | | 10/1991 |
| WO | WO 02/45574 | * | 12/2001 |
| WO | WO 02/45574 A2 | | 6/2002 |

* cited by examiner

Primary Examiner—Nicholas D. Lucchesi
Assistant Examiner—Matthew F DeSanto
(74) Attorney, Agent, or Firm—William J. Sapone; Coleman Sudol Sapone P.C.

(57) ABSTRACT

There is provided a needle device for percutaneous drug delivery to a patient. The device comprises a substantially L-shaped, hollow needle for drug delivery therethrough and a body. The needle includes a needle end and the body is secured to the needle and longitudinally spaced from the needle end. The body includes an integral pair of flexible handles adapted to be grasped for insertion of the needle device into and removal of the device from the patient.

11 Claims, 3 Drawing Sheets

DRUG DELIVERY NEEDLE DEVICE

FIELD OF THE INVENTION

This invention relates to a drug delivery needle and more specifically to a needle for percutaneous injection of a drug into an implanted drug delivery device having a catheter for drug delivery to a patient.

BACKGROUND OF THE INVENTION

Drug delivery devices are commonly implanted in a patient for long-term administration of drugs. These devices generally include a chamber with a self-sealing silicone septum and a catheter attached to the chamber and positioned for delivery of the drug to a suitable location, for example, into a vein. The chamber contains the drug for delivery to the patient through the catheter and is implanted such that the septum is located just under the skin of the patient. In order to access the chamber, the patient's skin and the septum of the drug delivery device are pierced using a needle and the drug is introduced into the chamber by injection using a syringe or other delivery device.

Conventional hypodermic needles are not used for the introduction of a drug to a drug delivery device for various reasons including, for example, the possibility that these needles can damage the septum. Instead, specially designed needles are used to pierce the skin and the septum. These needles include a right angle bend (approximately a ninety degree bend) for convenient access to the chamber and are designed to inhibit coring of the septum and ensure penetration of the skin and septum at approximately ninety degrees. The needles are appropriately sized to access the chamber of the device. A portion of the needle lies approximately parallel with the surface of the skin of the patient, to allow the needle to be taped down.

While they are an improvement over conventional needles, right-angle needles can still be somewhat difficult to hold and to push through the skin and the septum since the physician must firmly grasp the needle in order to drive the needle through the septum. Also, when taped down on the patient, prior art needles do not allow flow of air around the wound site. This can contribute to infection of the wound.

One particular prior art drug delivery needle is disclosed in U.S. Pat. No. 4,743,231, issued May 10, 1988 to Kay et al. This patent teaches a right angle drug administration needle with a rigid base for taping down to the skin of a patient and a releasably connectable handle for ease of handling. A foam pad extends around the periphery of the underside of the base and includes an adhesive surface for adhering to the skin of the patient. A low profile allows for the right angled needle device to be taped down to the user while the foam pad provides flow of air around the wound site.

Although this structure provides a handle for firmly grasping the needle and a foam pad for flow of air around the wound site, the drug delivery needle device still suffers from some disadvantages. The handle is molded separately from the remainder of the needle device and is releasable to provide a low profile when the device is taped down. Thus, when the tape is removed from the patient, the physician is required to find the handle and attach the handle to the base in order to remove the needle. Since the handle is removable, it can easily be misplaced or lost. Also, the base is rigid and does not conform to the skin surface of the patient.

Accordingly, it is an object of an aspect of the present invention to provide a drug delivery needle for percutaneous delivery of a drug into an implanted drug delivery device that obviates or mitigates at least one of the disadvantages of the prior art.

SUMMARY OF THE INVENTION

In one aspect of the present invention there is provided a needle device for percutaneous drug delivery to a patient. The device comprises a substantially L-shaped, hollow needle for drug delivery therethrough and a body. The needle includes a needle end and the body is secured to the needle and longitudinally spaced from the needle end. The body includes an integral pair of flexible handles adapted to be grasped for insertion of the needle device into and removal of the device from the patient.

Advantageously, the handles of the drug delivery device are attached to the remainder of the device. Also, the drug delivery device includes a spacer that spaces the handles away from the wound site when the drug delivery device is taped down on the patient. In an aspect of the invention, a portion of the L-shaped needle extends approximately from the center of a body between the pair of flexible handles. Thus, downward force on the body of the device is transmitted to the needle when the needle is inserted into the patient. This provides support and accuracy during insertion of the needle.

BRIEF DESCRIPTION OF THE DRAWINGS

The invention will be better understood with reference to the drawings, and following description, in which.

DETAILED DESCRIPTION OF PREFERRED EMBODIMENTS

Figure 1:
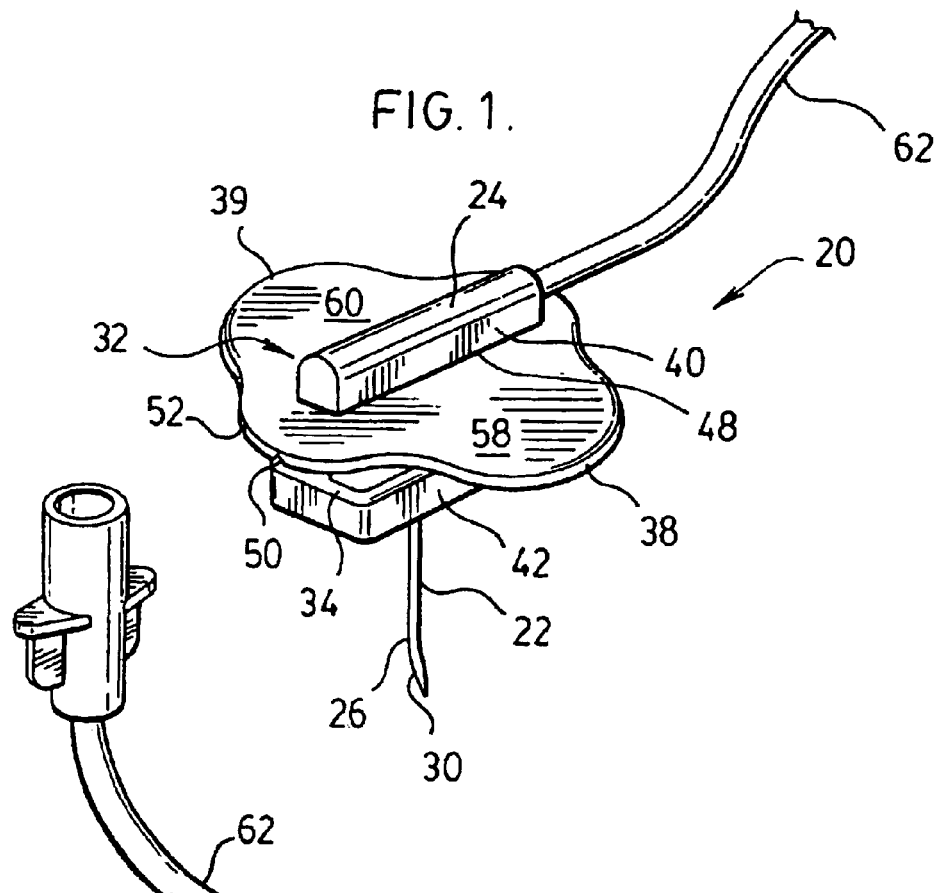
FIG. 1 is a perspective view of a needle device according to a preferred embodiment of the present invention.
Figure 2:
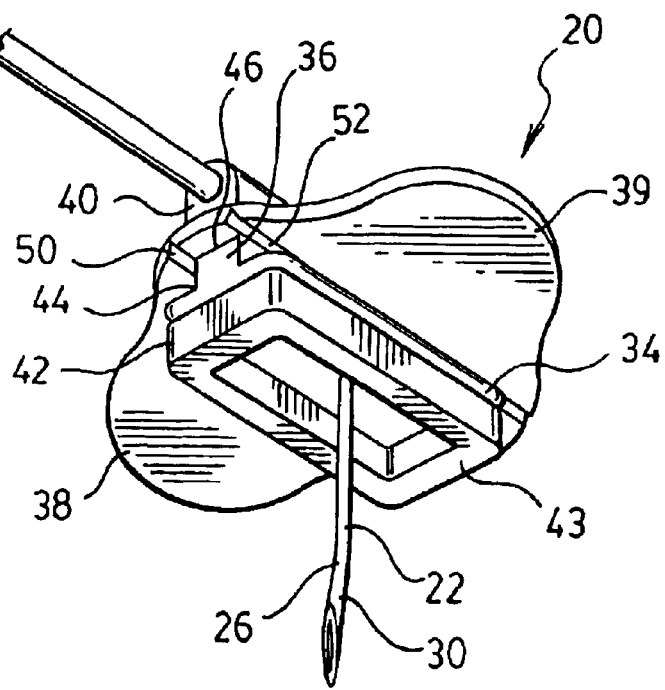
FIG. 2 is an alternative perspective view of the needle device of FIG. 1.

Reference is first made to FIGS. 1 and 2 to describe a preferred embodiment of a drug delivery needle device designated generally by the numeral 20. The drug delivery needle device includes a substantially L-shaped needle 22 for drug delivery therethrough. The needle 22 consists of first portion 24 and a second portion 26 with an included angle between the first portion 24 and second portion 26, forming the L-shape. In the present embodiment, the included angle is approximately ninety degrees. The needle 22 is hollow to define a continuous fluid passage through the first and second portions 24, 26, respectively. The first portion 24 of the needle 22 is attached to a flexible tube and will be described further below. The second portion 26 of the needle 22 includes a needle end 30 that is slightly bent with respect to the remainder of the second portion 26 and is longitudinally spaced from the first portion 24. The end 30 is bent to provide a non-coring needle, as will be understood by those of skill in the art. As shown in the figures, the continuous fluid passage is open at the needle end 30 and the needle end 30 is sharp for piercing the skin of a patient and for piercing a septum of a chamber of a catheter, for example.

A body 32 is molded of a resiliently flexible plastic around the first and second portions 24, 26, respectively. The body 32 includes a substantially rectangular base 34, a spacer 36, a pair of flexible handles 38, 39 and a cover 40, as discussed further below.

The substantially rectangular base 34 is molded around the second portion 26 and is longitudinally spaced from the end 30 such that the second portion 26 of the needle 22 passes through and extends from the base 34. A foam pad 42 extends around the periphery of one side of the base 34. The foam pad 42 is an open-celled plastic foam to allow air flow therethrough, thereby providing a layer that allows the flow of air between the molded plastic base 34 and the skin of a patient when in use. In the present embodiment, the foam pad and base are flexible for patient comfort.

Figure 3:
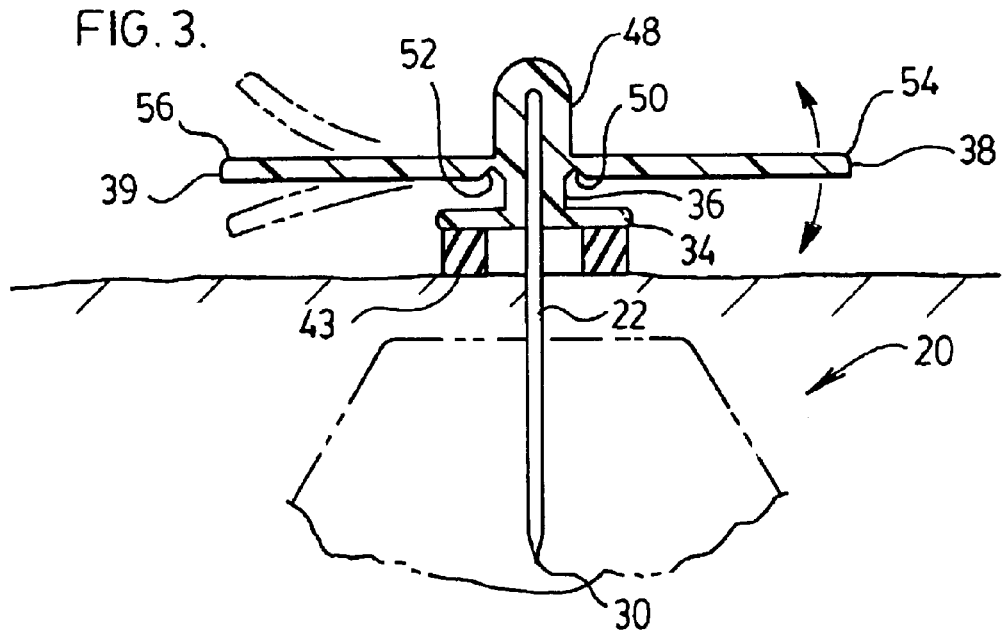
FIG. 3 is a cross-sectional front view of the needle device of FIG. 1 showing the device in use with a needle inserted into a chamber (shown in ghost outline) under the skin of a patient and showing a pair of handles, flexed in opposing directions in ghost outline.

One end 44 of the spacer 36 is coupled to a second side of the base 34 and the opposing end 46 is coupled to the cover 40. It can be seen that the first portion 24 of the needle 22 extends through the cover 40 such that the cover 40 and the first portion 24 form a rigid spine 48 that provides rigidity for the device 20. The second portion 26 of the needle 22 extends through the spacer 36 and the base 34. As shown in FIGS. 1, 2 and 3, the second portion 26 of the needle 22 extends longitudinally and is approximately perpendicular to the base 34, while the spine 48 is approximately parallel with the base 34.

Figure 5:
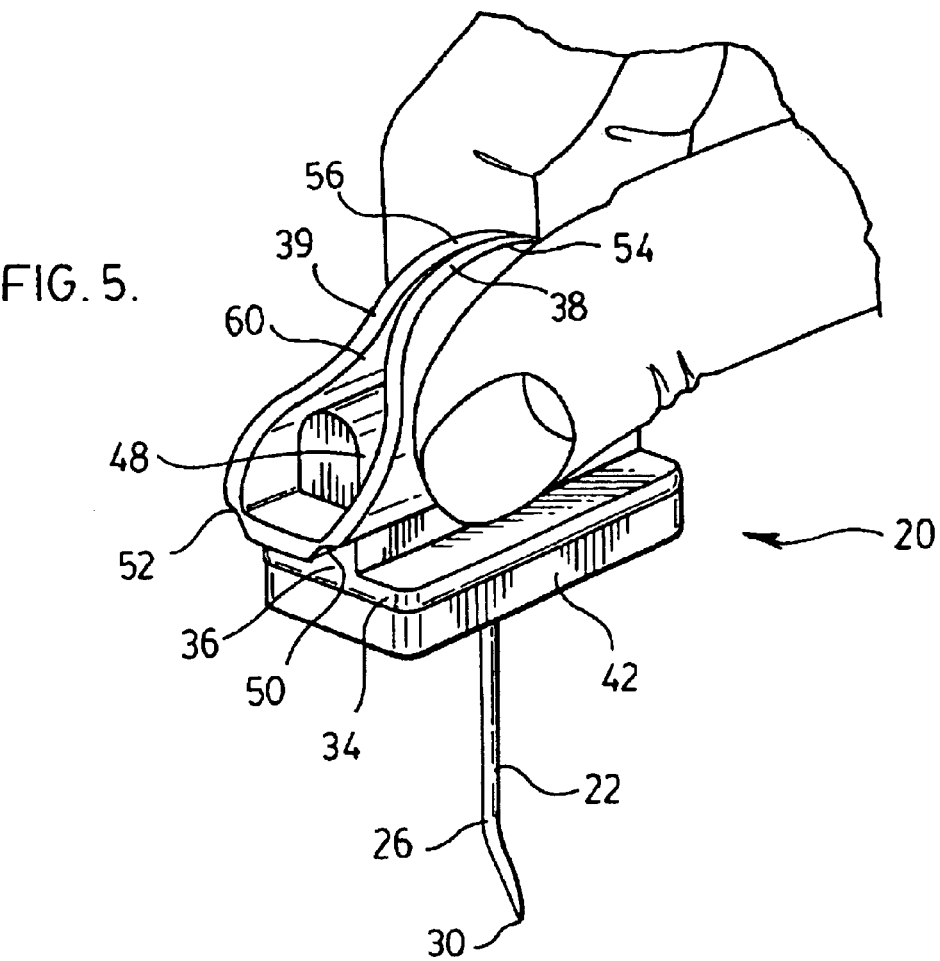
FIG. 5 is a perspective view of the needle device of FIG. 1, showing the handles being grasped.
Figure 6:
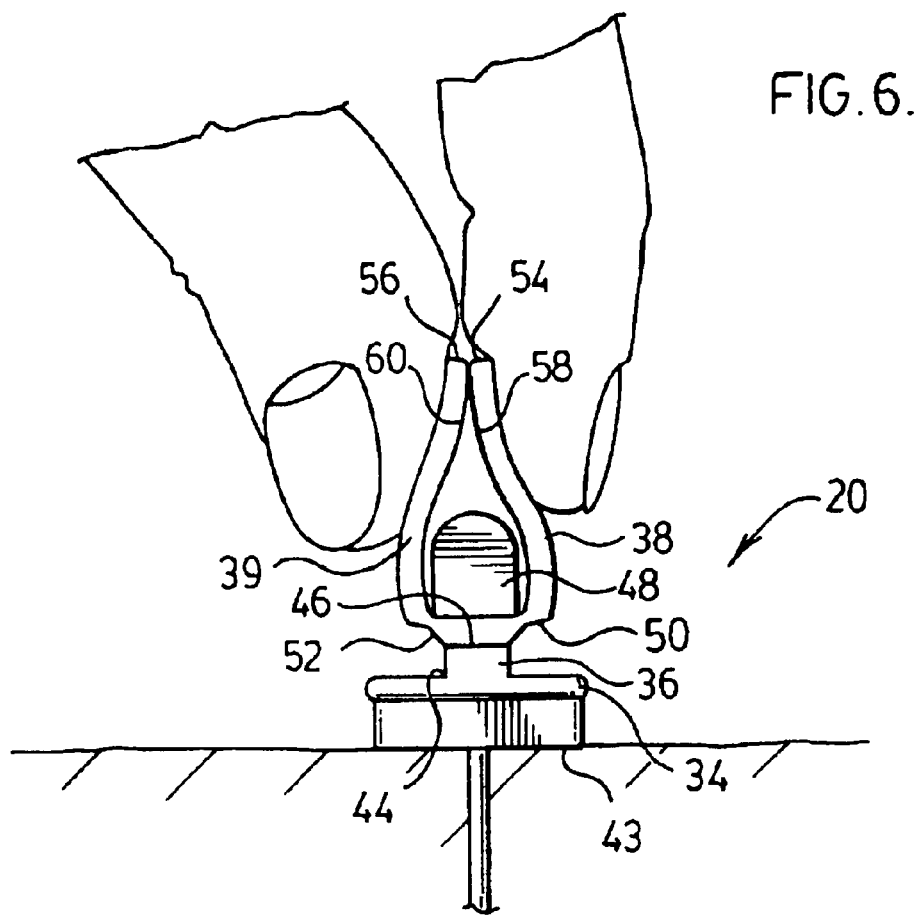
FIG. 6 is a front view of the needle device of FIG. 5, showing the handles being grasped.
Figure 4:
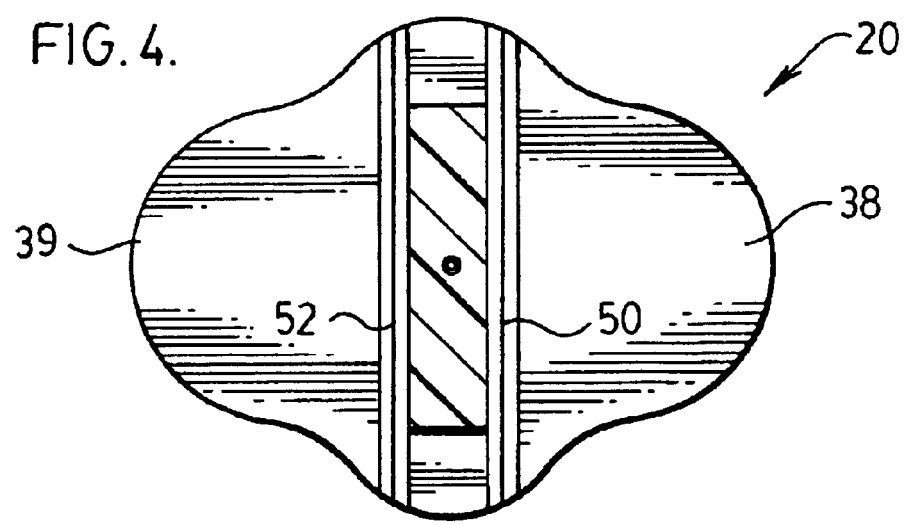
FIG. 4 is a bottom view of the needle device of FIG. 1, showing the needle in cross-section.

Referring to FIG. 3, each of the flexible handles 38, 39 extends laterally from and is coupled to the spine 48 such that the spine 48 is located between the handles 38, 39. The spine 48 effectively couples the handles 38, 39 to the spacer 36 which spaces the handles 38, 39 from the base 34. Each of the handles 38, 39 includes a groove 50, 52, respectively, extending along the width of the handles 38, 39, adjacent the spine 48. The handles 38, 39 also include distal ends 54, 56, respectively, that are laterally spaced from the spine 48 and the grooves 50, 52. These grooves 50, 52 provide a thin region in comparison with the remainder of the handles 38, 39. This provides increased flexibility in this region. In order to grasp the device 20, the handles 38, 39 are flexed away from the base 34 such that backsides 58, 60 of each of the respective handles 38, 39 are in contact with each other at the distal ends 54, 56. Thus, the handles 38,39 are effectively pinched together when grasped, as best shown in FIGS. 5 and 6. When no longer grasped, the handles 38, 39 return to their laterally extending state. As shown in the Figures, the second portion 26 of the needle 22 extends approximately from the center of the body 32, between the pair of flexible handles, 38, 39.

The handles 38, 39 can also flex in the opposite direction. It will be appreciated that the handles 38, 39 are spaced from the base 34 in order to inhibit contact of the handles 38, 39 with a patient's skin proximal the wound site when the device 20 is in use.

Referring again to FIG. 1, a flexible tube 62 is connected to and in fluid communication with the first portion 24 of the needle 22. The tube 62 extends outwardly from the spine 48. The flexible tube 62 is made of a suitable plastic for delivery of a drug through the tube 62, into the first portion 24 of the needle.

Although each of these elements are described separately, it will be appreciated that in the present embodiment the base 34, the spacer 36, the handles 38, 39 and the cover 40 are a unitary molded plastic.

The use of the drug delivery device 20 will now be described with reference to FIGS. 3 to 6. For the purpose of the present description, a chamber with a self-sealing septum, shown in ghost outline in FIG. 3, is implanted such that the chamber is located just under the skin of the patient. The chamber is designed to contain the drug for delivery to the patient through a catheter. The use of a chamber and self-sealing septum is understood in the art and will not be further described herein.

In order to access the chamber, the patient's skin and the septum are pierced using the device 20. To accomplish this, the handles 38, 39 of the device 20 are flexed by pinching the handles 38, 39, preferably between the thumb and the forefinger, such that they are in contact with each other at the distal ends 54, 56 of the backsides 58, 60, as shown in FIGS. 5 and 6. Next, the needle end 30 is positioned at the desired location on the skin of the patient (at the location of the self-sealing septum). Pressure is then applied towards the surface of the skin causing the end 30 of the needle 22 to puncture the skin and the self-sealing septum of the chamber. It will be appreciated that the spine 48 provides rigidity to the device 20 when the needle 22 is being inserted or extracted from a patient. As stated above, the second portion 26 of the needle 22 extends approximately from the center of the body 32, between the pair of flexible handles, 38, 39. The needle is inserted until the foam pad 42 is adjacent the patient's skin. With the needle end 30 located in the chamber, the fluid or drug is then delivered to the chamber through the flexible tube 62, through the first and second portions 24, 26, respectively and out the needle end 30.

It may be desirable to leave the device 22 with the end 30 of the needle 22 inserted into the chamber for a long period of time. In such case, the device is generally taped to the skin of the patient. Thus, the handles 38, 39 are flexed in the direction of the skin of the patient. Since the spacer 36 spaces the handles 38, 39 from the base 34, the handles are effectively inhibited from contacting the skin of the patient immediately around the foam pad 42 on the base 34. The foam pad 42 allows for the flow of air around the wound site (where the needle puncture is located).

To remove the device 20, any tape that has been used to secure the device 20 is first removed. The handles 38, 39 are then grasped, as discussed above, and pulled outwardly, away from the patient. Thus, the needle 22 is removed from the patient and the septum of the chamber seals.

While the embodiment discussed herein is directed to a particular implementation of the present invention, it will be apparent that variations and modifications to this embodiment are possible. For example, the L-shaped needle can have any suitable included angle and can vary from ninety degrees. Also, the body structure described above does not need to be a unitary molded structure and can be individual pieces coupled together. The size and shape of many of the parts can vary while still performing the same function. All of these variations and modifications are within the scope sphere of the invention as defined by the claims appended hereto.

What is claimed is:

1. A needle device for percutaneous drug delivery to a patient, the device comprising: a substantially L-shaped, hollow needle for drug delivery therethrough, the needle device including a base, a spacer having first and second ends that are longitudinally spaced apart, said first end being integral with said base, and a pair of opposed flexible handles integral with said second end of said spacer, the flexible handles adapted to be grasped for insertion of said needle device into and removal of said needle device from said patient, a rigid spine located above the spacer and the handles, the rigid spine including a first portion of said L-shaped needle therein, which extends substantially parallel to said base, a second portion of said L-shaped needle extends substantially perpendicular to said base, said second portion passing through said rigid spine and spacer to extend downwardly from said base, the handles having distal ends movable into contact with each other when the handles are grasped, the handles engaging said spine when said distal ends are in contact.

2. The needle device according to claim 1 wherein said base is flexible for conforming to a skin surface of a patient.

3. The needles device according to claim 2 further comprising a breathable pad on said base for contact with said skin surface of said patient.

4. The needle device according to claim 3 wherein said breathable pad extends around the periphery of said base.

5. The needle device according to claim 4 wherein said breathable pad is a plastic foam pad.

6. The needle device according to claim 1 wherein said handles are flexible away from said base for grasping.

7. The needle device according to claim 6 wherein each of said handles includes a groove extending along a width of said handles for increased flexing in a preferred region of said handles.

8. The needle device according to claim 7 wherein said groove is v-shaped.

9. The needle device according to claim 1 wherein said portion of said needle extends approximately from a center of said base.

10. The needle device according to claim 1 wherein said spine includes a needle cover, said needle cover covering at least a portion of said first portion of said needle, said cover being unitary with said spacer, said base and said handles.

11. The needle device according to claim 1 further comprising a flexible tube having one end coupled to and in fluid communication with an end of said first portion of said needle.

* * * * *